(12) United States Patent
Reynolds et al.

(10) Patent No.: US 12,109,323 B2
(45) Date of Patent: *Oct. 8, 2024

(54) INDOOR LIGHTING APPARATUS INCLUDING ULTRAVIOLET LIGHT SOURCE

(71) Applicant: CH Reynolds Electric Inc., San Jose, CA (US)

(72) Inventors: Chuck Reynolds, San Jose, CA (US); Mark Hiura, San Jose, CA (US)

(73) Assignee: CH Reynolds Electric Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/987,752

(22) Filed: Nov. 15, 2022

(65) Prior Publication Data

US 2023/0082999 A1    Mar. 16, 2023

Related U.S. Application Data

(63) Continuation of application No. 17/364,644, filed on Jun. 30, 2021, now Pat. No. 11,541,137.

(Continued)

(51) Int. Cl.
*A61L 2/10* (2006.01)
*A61L 9/20* (2006.01)
*F21S 8/04* (2006.01)
*F21V 23/04* (2006.01)
*H05B 47/115* (2020.01)

(Continued)

(52) U.S. Cl.
CPC .................. *A61L 2/10* (2013.01); *A61L 9/20* (2013.01); *F21S 8/046* (2013.01); *F21V 23/0471* (2013.01); *H05B 47/115* (2020.01); *H05B 47/155* (2020.01); *H05B 47/16* (2020.01); *A61L 2202/11* (2013.01); *A61L 2202/14* (2013.01); *A61L 2202/25* (2013.01);

(Continued)

(58) Field of Classification Search
CPC .......... A61L 2/10; A61L 9/20; A61L 2202/11; A61L 2202/14; A61L 2202/25; A61L 2209/111; A61L 2209/12; H05B 47/115; H05B 47/16; H05B 47/155; F21S 8/046; F21V 23/0471; F21Y 2113/10; F21Y 2115/10

See application file for complete search history.

(56) References Cited

U.S. PATENT DOCUMENTS 10,794,082 B1 * 10/2020 Watson ............... F21V 23/0471
10,808,964 B2 * 10/2020 Polidoro ................ F21S 8/033

(Continued)

*Primary Examiner* — Bao Q Truong

(57) ABSTRACT

An overhead lighting fixture containing both visible light sources and UV light sources is disclosed herein. UV light can sanitize/disinfect the surrounding environment after the environment over a period of about 30-45 minutes. In this way, viruses, germs, bacteria, mold, and the like can be destroyed to clean the air and/or surfaces (e.g., furniture). Accordingly, embodiments of the present invention provide a controllable UV lighting assembly that can produce UV light to sanitize/disinfect an area and can be automatically disabled to prevent UV light exposure to those in the area using a motion sensor. The lighting assembly can produce visible light while the UV light source is disabled. According to some embodiments, the duration of UV light production is controlled by a timer for power savings.

20 Claims, 6 Drawing Sheets

Related U.S. Application Data

(60) Provisional application No. 63/047,795, filed on Jul. 2, 2020.

(51) Int. Cl.
    *H05B 47/155*    (2020.01)
    *H05B 47/16*     (2020.01)
    *F21Y 113/10*    (2016.01)
    *F21Y 115/10*    (2016.01)

(52) U.S. Cl.
    CPC ...... *A61L 2209/111* (2013.01); *A61L 2209/12* (2013.01); *F21Y 2113/10* (2016.08); *F21Y 2115/10* (2016.08)

(56) References Cited

U.S. PATENT DOCUMENTS

| | | | |
|---|---|---|---|
| 11,541,137 B2 * | 1/2023 | Reynolds | H05B 47/115 |
| 2011/0187273 A1 * | 8/2011 | Summerford | H05B 47/10 |
| | | | 315/250 |
| 2018/0320872 A1 * | 11/2018 | Weeks, Jr. | A61L 2/084 |

\* cited by examiner

INDOOR LIGHTING APPARATUS INCLUDING ULTRAVIOLET LIGHT SOURCE

CROSS-REFERENCE TO RELATED APPLICATIONS

This application claims the benefit of and priority to copending patent application Ser. No. 17/364,644, with filing date Jun. 30, 2021, and to provisional patent application Ser. No. 63/047,795, entitled "INDOOR LIGHTING APPARATUS INCLUDING ULTRAVIOLET LIGHT SOURCE," with filing date Jul. 2, 2020, both of which are hereby incorporated by reference in their entirety as if fully set forth below.

FIELD

Embodiments of the present invention generally relate to the field of lighting fixtures. More specifically, embodiments of the present invention relate to apparatus and methods drawn to a light fixture or lighting assembly having antiviral properties and capable of being disposed indoor or outdoor.

BACKGROUND

It is well-known that viruses, germs, bacteria, mold, and the like present a public health concern. Currently homes, businesses, and public areas are sanitized using chemicals sprayed onto surfaces and wiped away to clean the surfaces and destroy any pathogens thereon. However, this approach is time consuming, inefficient, costly, and fails to address airborne pathogens thereon that are not resting on a surface.

Recently solutions to sanitize and sterilize indoor environments incorporate the use of UV lights to destroy pathogens that may be airborne or resting on surfaces that are exposed to the UV light. However, these approaches currently rely on existing power and control systems which are not well-suited for sanitation using UV light. For example, activating UV lighting in a room occupied by people can potentially harm the occupant's skin, eyes, etc. Moreover, these lighting systems are typically controlled manually using a traditional switch which often leads to UV lights being activated during times when they are not necessarily needed or potentially dangerous to the room's occupants. A safer and more efficient light module and approach to sanitation using UV lighting are needed.

SUMMARY

A lighting fixture containing both visible light sources and UV light sources is disclosed herein. In one embodiment, the fixture is an overhead fixture. UV light can sanitize/disinfect the surrounding environment over a period of about 30-45 minutes. In this way, viruses, germs, bacteria, mold, and the like can be destroyed to clean the air and/or surfaces (e.g., furniture) of the room exposed to UV light. Accordingly, embodiments of the present invention provide a controllable UV lighting assembly or fixture that can produce UV light to sanitize/disinfect an area and can be automatically disabled to prevent UV light exposure to those in the area using a motion sensor. The lighting assembly may contain a visible light source and therefore can produce visible light while the UV light source is disabled. According to some embodiments, the duration of UV light production is controlled by a timer for power savings.

According to one embodiment, a method of automatically disabling an ultraviolet (UV) light source of a lighting assembly is disclosed. The method includes closing a relay of the lighting assembly to power the UV light source of the lighting assembly, the lighting assembly includes a visible light source and the UV light source, and opening the relay to power the visible light source to produce visible light so that the opening also correspondingly shuts off the UV light source.

According to some embodiments, the method includes determining that a timer associated with the lighting assembly expired and the opening further includes opening the relay responsive to the determining that the timer expired.

According to some embodiments, the lighting assembly is operable to be an overhead lighting assembly for installation in a ceiling of an indoor environment.

According to some embodiments, the visible light source includes at least one of: a plurality of fluorescent lights and a plurality of visible light LED lights.

According to some embodiments, the UV light source includes a UV LED emitter.

According to some embodiments, the method includes opening the relay to power the visible light source to produce visible light, the opening also correspondingly shuts off the UV light source, and the opening is responsive to data produced by a sensor.

According to a different embodiment, a lighting assembly is disclosed, including a first light source configured to produce a first light, a second light source configured to produce a second light, and control circuitry for selectively powering the first light source and the second light source. The control circuitry includes a sensor, a relay coupled to the sensor and for selectively coupling a power source to one of: the first light source and second light source, and a timer. The control circuitry automatically controls the relay to couple the relay to the first light source when the timer expires, automatically controls the relay to couple the relay to the second light source when the timer is active, and automatically controls the relay to couple the relay to the first light source according to a reading of the sensor.

According to some embodiments, the lighting assembly is operable to be an overhead lighting assembly for installation in a ceiling of an indoor environment.

According to some embodiments, the first light source includes at least one of: a plurality of fluorescent lights and a plurality of visible light LED lights.

According to some embodiments, the second light source includes a UV LED emitter.

According to some embodiments, the lighting assembly further includes an external switch and an external power source for powering the first light source, and activating the external switch activates the first light source.

According to some embodiments, the lighting assembly includes a housing and the motion sensor is integrated into the housing.

According to some embodiments, the timer is controlled by a remote wireless device.

According to another embodiment, a lighting assembly is disclosed. The lighting assembly includes a first light source configured to produce a first light type, a second light source configured to produce a second light type, and control circuitry for selectively powering the first light source and the second light source. The control circuitry includes a sensor, a wireless transceiver, and a timer. The control circuitry automatically receives a timer value from a wireless device using the wireless transceiver, controls the relay to couple the relay to the first light source when the timer value expires, automatically controls the relay to couple the relay to the second light source when the timer is active, and automatically controls the relay to couple the relay to the first light source according to a reading of the sensor.

According to some embodiments, the lighting assembly includes a safety timer that defines a safe period for the second light source, the control circuitry controls the relay to couple the relay to the second light source only when both the timer and the safety timer are active.

According to some embodiments, the lighting assembly includes a third light source, the control circuitry controls the relay to couple the relay to the first light source and the third light source when the timer value expires.

According to some embodiments, the lighting assembly is operable to be an overhead lighting assembly for installation in a ceiling of an indoor environment.

According to some embodiments, the first light source includes at least one of: a plurality of fluorescent lights and a plurality of visible light LED lights.

According to some embodiments, the second light source includes a UV LED emitter.

According to some embodiments, the second light source produces a type of a light spectrum that kills viruses, germs, bacteria, and mold using a specific frequency of UV light or a specific duration of exposure.

DETAILED DESCRIPTION

Figure 1:
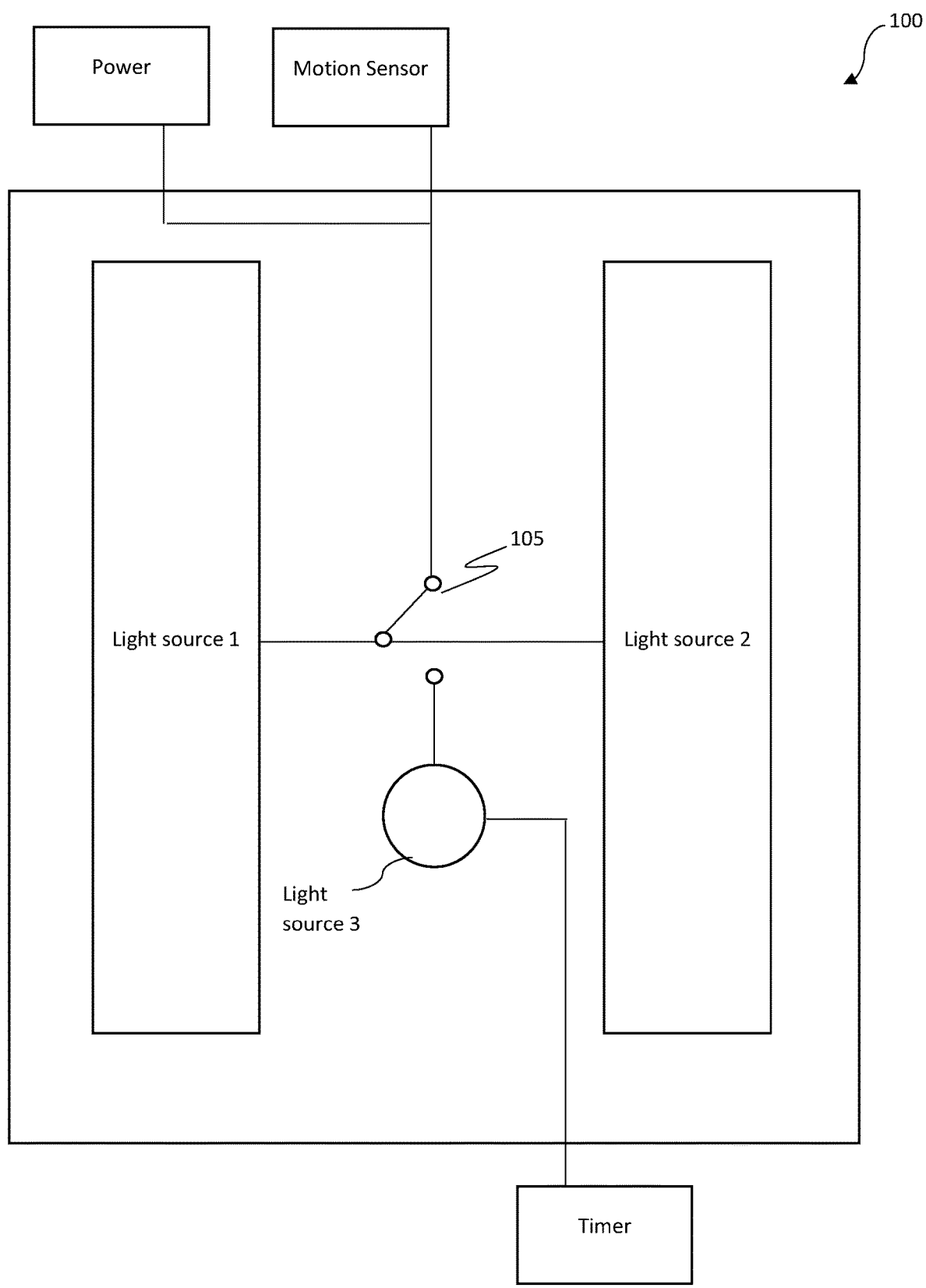
FIG. 1 depicts an exemplary lighting assembly or fixture with a presently open relay according to embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follows are presented and discussed in terms of a method. Although steps and sequencing thereof are disclosed in a figure herein (e.g., FIGS. 5-6) describing the operations of this method, such steps and sequencing are exemplary. Embodiments are well suited to performing various other steps or variations of the steps recited in the flowchart of the figure herein, and in a sequence other than that depicted and described herein.

Indoor Lighting Apparatus Including Ultraviolet Light Source

According to embodiments of the present invention, a lighting fixture or assembly is described that contains a light source that produces ultra-violet (UV) light, such as an LED, for example. UV light can be of any of a number of well-known UV source types and can sanitize/disinfect the surrounding environment if left on over a period of about 30-45 minutes. In this way, viruses, germs, bacteria, mold, and the like that are on the surfaces nearby and exposed to the UV light can be destroyed to clean the air and/or surfaces (e.g., furniture). Accordingly, embodiments of the present invention provide a controllable UV lighting assembly that can produce UV light to sanitize/disinfect an area and can be automatically disabled to prevent UV light exposure to people in the area using a motion sensor and/or other signal inputs. The lighting assembly can also provide visible light by containing visible light emitting bulbs and/or LED elements in addition to the UV light LED. In most embodiments, the visible light is provided while the UV light source is disabled since UV light is not generally advised while a room is occupied. According to some embodiments, the UV light can be triggered "on" by a motion sensor (e.g., lack of motion for a prescribed period) and the duration of UV light production is further controlled by a timer (e.g., an electronic or adjustable timer) for power savings. Since visible light emission and UV light emission within the fixture are generally on at different times, a common relay can be used to control both the UV LED and the visible light bulb(s), in one embodiment.

FIG. 1 depicts an exemplary lighting assembly or fixture 100 with a presently open relay 105 according to embodiments of the present invention. In this embodiment, the power source and motion sensor are remote to fixture 100. The relay can be controlled (opened/closed) by selectively energizing an electromagnet in the relay using a power source in one embodiment.

Lighting assembly 100 produces visible light using Light source 1 and/or Light source 2. Two visible light emitters are shown but this is exemplary only, as the light fixture 100 can include fewer or more visible light emitters. Light source 1 and Light source 2 are coupled to light couplings that both secure the lights and also conduct power to the lights; Light source 1 and Light source 2 can include fluorescent overhead lights, LED lighting arrays, or any suitable light source configured to provide visible light. Light source 3 on the other hand is a light source configured to produce UV light, such as an LED and is secured by light couplings which also conduct power to Light source 3 and can be used to secure Light source 3. Any suitable means for producing UV light can be used.

The UV light as is known cleans and/or disinfects the environment generally nearby the lighting fixture 100, e.g., about 20 feet from the fixture, over a period of exposure equal to about 30-45 minutes. The duration of the UV light produced by Light source 3 can be controlled by a timer and/or a motion detector. For instance, if no motion is detected over a period of time by the motion detector, then the UV light source can be turned on. The timer can be set for a predetermined duration (e.g., 30-45 minutes), or can include a dial or other input device that can be used to set a duration for producing UV light. During the "on" duration period of the UV light, any motion detected by the motion detector would shut off the UV light and turn off the UV "on" period. The timer signal can be used to provide the desired amount of UV light and another timer signal can also be used to prevent the UV light from being active when people are expected to enter the environment (e.g., an office, store, home, or other similar indoor environment) during work hours, for example. Saying this another way, a timer signal can be used as an override to only allow the UV "on" duration during those hours when people are not expected to be in the room, e.g., after regular work hours of an office or during expected sleep periods of a home.

Lighting assembly 100 includes relay 105 for selectively powering Light source 1 and Light source 2 to produce visible light and Light source 3 to provide UV light. The relay 105 is coupled to a power source and a motion sensor that can selectively open/close the relay when motion is detected to produce visible light (and turn off Light source 3) for the detected person/motion. For example, as depicted in FIG. 1, relay 105 is configured in the open position to provide power to Light source 1 and Light source 2. It is appreciated that Light source 3 is not powered when relay 105 is configured in this way as UV light is not advised when people are present. Therefore, in the condition when motion is detected, the lighting assembly 100 does not produce UV light and the environment is lit with visible light and is safe for occupants.

When the motion sensor does not detect motion for a prescribed period of time, the room is assumed to be empty, and the motion sensor can cause relay 105 to close. According to some embodiments, relay 105 is a normally closed relay that remains closed until toggled by the motion sensor. When relay 105 is closed, Light source 3 can be powered to produce UV light. The UV light can be further controlled by a timer signal so that the UV light is only produced when the timer is active (not yet expired) and defines a UV "on" duration. The timer can be a circuit including an input device for setting the duration of the timer, an electronically controllable timer, and/or a fixed/preset timer. The timer that defines the UV "on" duration can be integrated within the fixture 100, or it can be external to the fixture with a signal line input to the fixture. In this embodiment, the UV "on" duration does not trigger unless motion has not been detected for the prescribed period. The UV on duration will terminate upon the motion detector detecting motion.

It is further appreciated that the UV "on" duration can be further activated as described above, by another (second) timer signal which defines periods when people are not expected to be present, e.g., off work hours or sleep home hours. In this embodiment, the UV "on" duration will not start unless 1) motion has not been detected over the prescribed period AND 2) the second timer indicates a safe period, e.g., people are not expected to be present. When 1) and 2) are satisfied, in this embodiment, then the UV on period starts and will run for the timer duration unless motion is detected again. It is appreciated that the source of the second timer can be integrated within the fixture 100 or it can be generated externally with a signal supplied to the fixture 100.

According to some embodiments, lighting assembly 100 includes additional relays/circuitry so that Light source 1 and Light source 2 can be powered or activated separately. For example, only one of Light source 1 and Light source 2 can be powered to provide half of the visible light that can be produced by lighting assembly 100, and both of Light source 1 and Light source 2 can be powered at the same time to provide the full amount of visible light. In other embodiments Light source 1 and Light source 2 are also dimmable.

According to some embodiments, Light source 1 and Light source 2 are a single light source.

Figure 2:
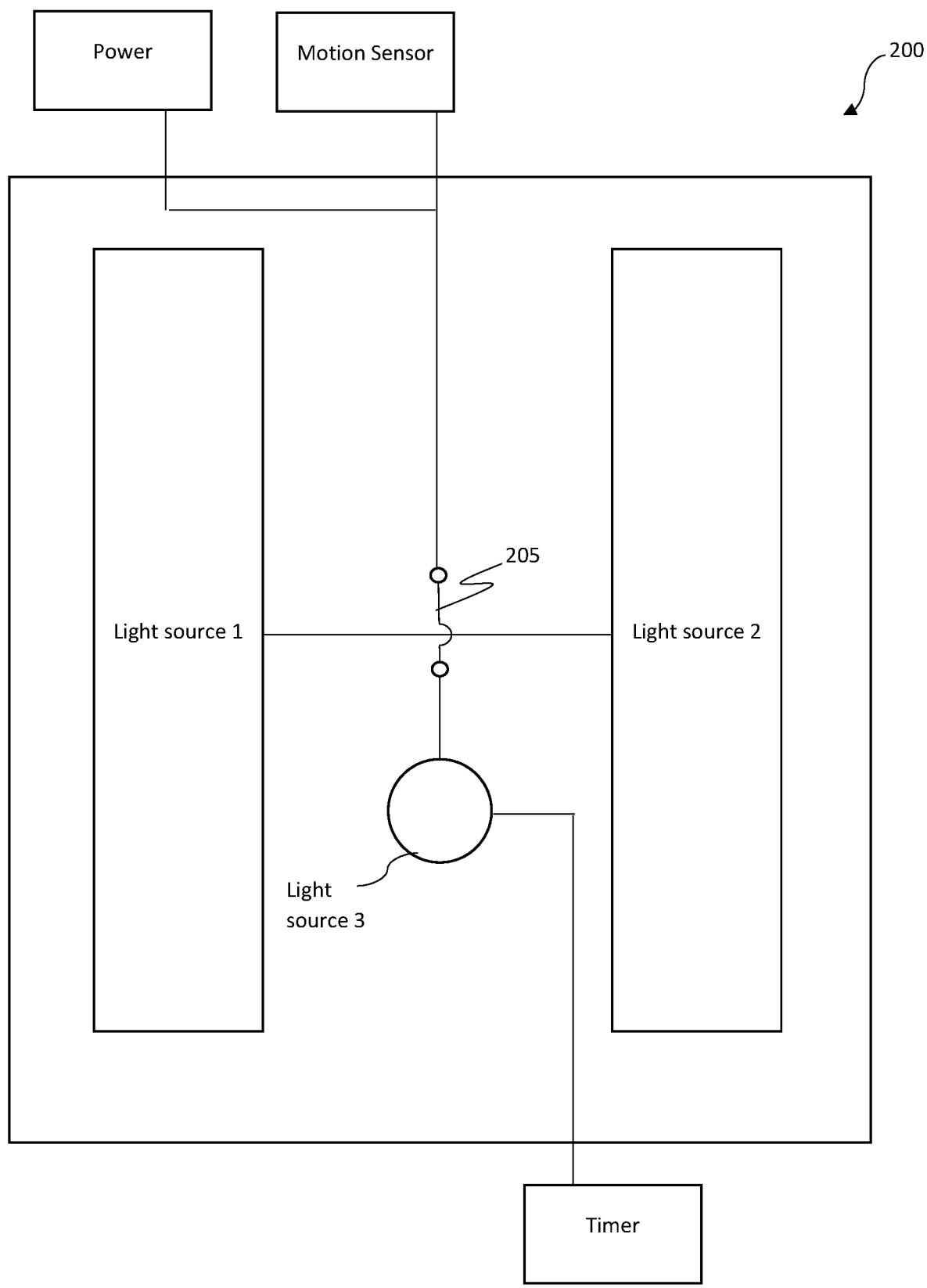
FIG. 2 depicts a lighting assembly including a presently closed relay depicted according to embodiments of the present invention.

FIG. 2 depicts a lighting assembly 200 including a presently closed relay 205 according to embodiments of the present invention. In this state, the relay 205 is closed to power/activate Light source 3 for providing UV light to clean/disinfect the environment. As mentioned above, Light source 3 can also be controlled by one or more timers for setting a duration of UV light production and a safe time period in which the UV can be activated and otherwise it is inhibited. FIG. 2 also shows the remote motion sensor.

Figure 3:
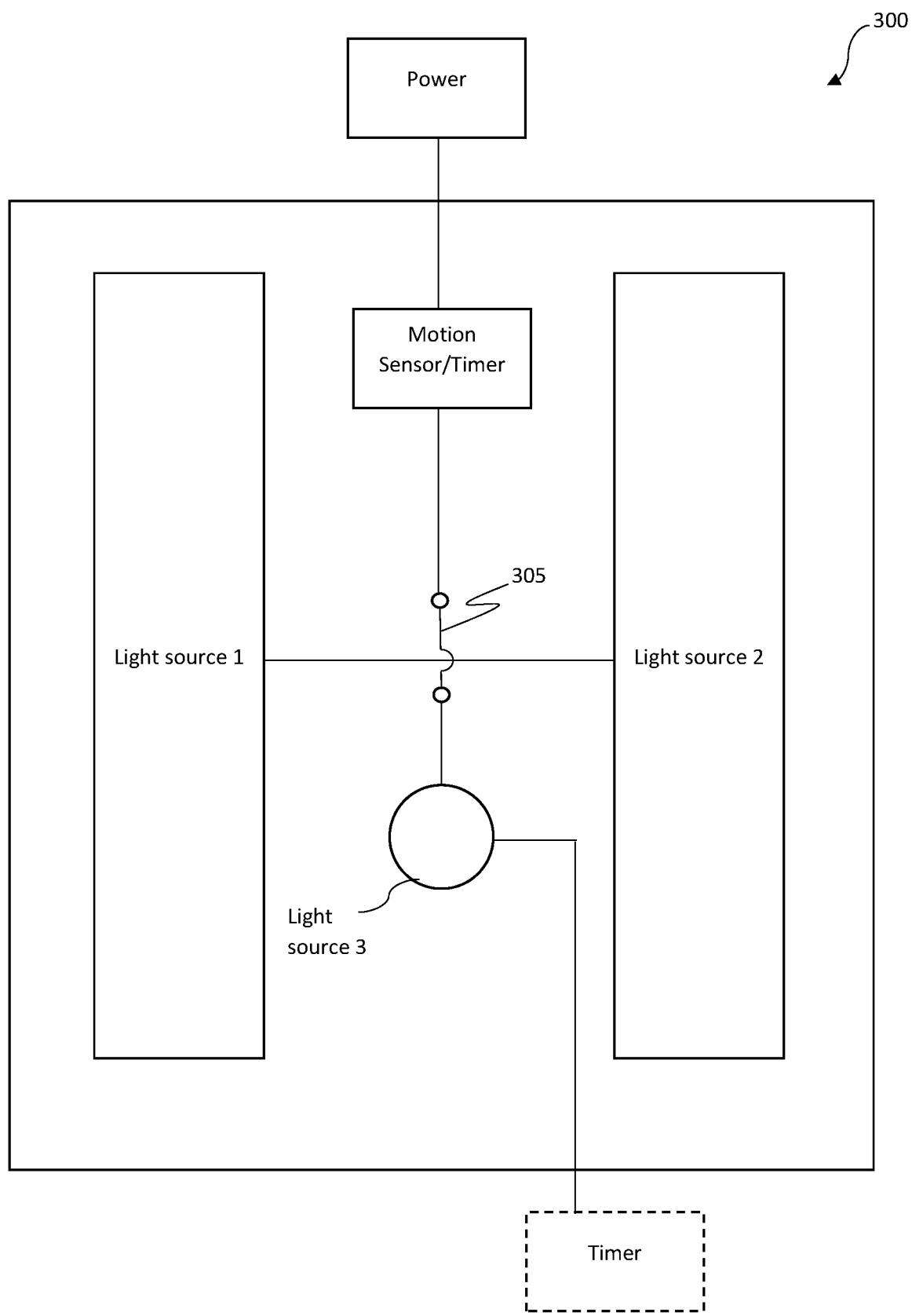
FIG. 3 depicts a lighting assembly including an integrated motion sensor/timer according to embodiments of the present invention.

FIG. 3 depicts a lighting assembly 300 including an integrated motion sensor/timer according to embodiments of the present invention. The motion/sensor timer is powered by an external power source and uses a motion sensor internal to the lighting assembly 300. The internal motion sensor can activate Light source 3 to provide UV light when no motion is detected over a prescribed period by closing relay 305, and can disable Light source 3 when motion is detected by opening relay 305. The motion sensor can include an integrated timer for controlling a duration of UV light production, e.g., the UV "on" duration, or can use a remote timer, for example, using wireless electronic communication (e.g., Wi-Fi, Bluetooth, etc.). The lighting assembly 300 can optionally include an internal second timer for controlling or defining the safe period in which the "on" duration of UV light produced by Light source 3 is allowed as discussed above with regard to FIGS. 1-2.

Figure 4:
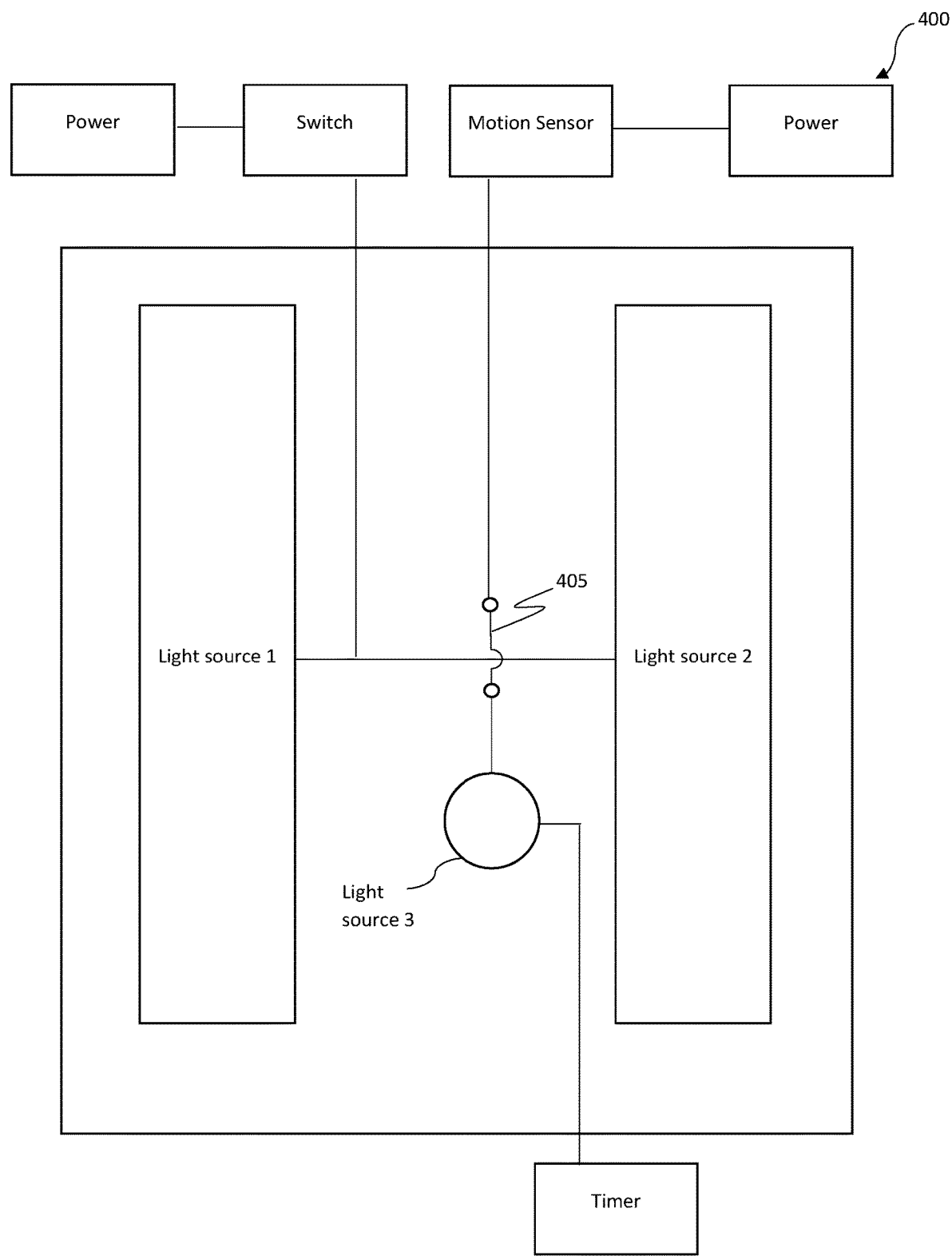
FIG. 4 depicts a lighting assembly including an external switch for controlling lighting assembly according to embodiments of the present invention.

FIG. 4 depicts a lighting assembly 400 including an external switch for controlling lighting assembly 400 according to embodiments of the present invention. The external switch is powered to turn Light source 1 and Light source 2 on and off selectively and/or to provide dimming. The motion sensor is powered separately from the external switch and selectively provides power to Light source 3 for producing UV light when relay 405 is closed. The motion sensor can activate Light source 3 to provide UV light (when no motion is detected after a prescribed period of time) by closing relay 405, and can disable Light source 3 when motion is detected (or when the "on" duration of UV light expires) by opening relay 405. As mentioned, the UV light can be further controlled by a timer so that the UV light is only produced when the timer is active (not expired). The timer can be a circuit including an input device for setting the duration of the timer, an electronically controllable timer, and/or a fixed/preset timer.

The embodiment depicted in FIG. 4 can include additional relays/circuitry to prevent lighting assembly 400 from receiving power from both power sources at the same time. According to some embodiments, the different power sources provide different voltages (e.g., 120V, 277V, low voltage, etc.) as the visible light emitters can operate at different voltages from the UV light emitter (Light source 3).

According to another embodiment, an overhead lighting fixture includes a frame, power couplings ("first power couplings") coupled to said frame and for physically retaining and powering a plurality of visible lights, and another set of power couplings (second power couplings) coupled to said frame and for physical retaining and powering a UV light. The overhead lighting fixture also includes a power input and a relay coupled to said power input and for selectively providing power to said first and second power couplings. The overhead lighting fixture can selectively provide power to the one power coupling and disable power to the other power coupling. The overhead lighting fixture can include a motion detector input for receiving a motion detector signal, and a timer input for receiving a timer signal, said timer signal is triggered to start upon said motion detector signal indicating no motion for a prescribed period. The relay is controlled to provide power to the first power coupling and disable power to said second power couplings when said motion detector signal indicates motion, and said relay is controlled to provide power to said second power coupling and disable power to said first power couplings when the motion detector signal indicates no motion and said timer has not expired.

According to some embodiments, the timer and the motion detector are integrated into the overhead lighting fixture.

According to some embodiments, the overhead lighting fixture includes another timer input (second timer input) to receive a second timer signal which is an override and indicates a safe period in which said second couplings can be enabled. The relay is controlled to provide power to the second power coupling and to disable power to the first power couplings when the motion detector signal indicates no motion, the timer has not expired, and the second timer signal is active (not expired). According to some embodiments, the lighting fixture includes a controller to control the relay. When motion is detected, the controller can provide power to the first power couplings and disable power to the second power couplings. The controller can provide power to the second power couplings when no motion is detected for a period of time, the timer input is active, and the second timer signal indicates that it is safe to provide power to the second power couplings. The controller can reset the first timer when no motion is detected for a prescribed period of time and the second timer indicates that it is safe to provide power to the second power couplings.

According to some embodiments, multiple lighting assemblies are used in conjunction. For example, multiple lighting assemblies can be installed in the same room and controlled by a single timer and/or motion sensor. Depending on the size of a room and the strength of the UV emitter, a determination can be made as to the number of lighting fixtures (and placement thereof) that a particular room requires for adequate sanitation. It is appreciated that the dimensions of the lighting fixtures in accordance with embodiments of the present invention can be sized such that they are analogous to commercially available office lighting fixtures.

According to some embodiments, the UV light source is customized to kill viruses, germs, bacteria, and/or mold using a specific frequency of UV light or a specific duration of exposure.

Figure 5:
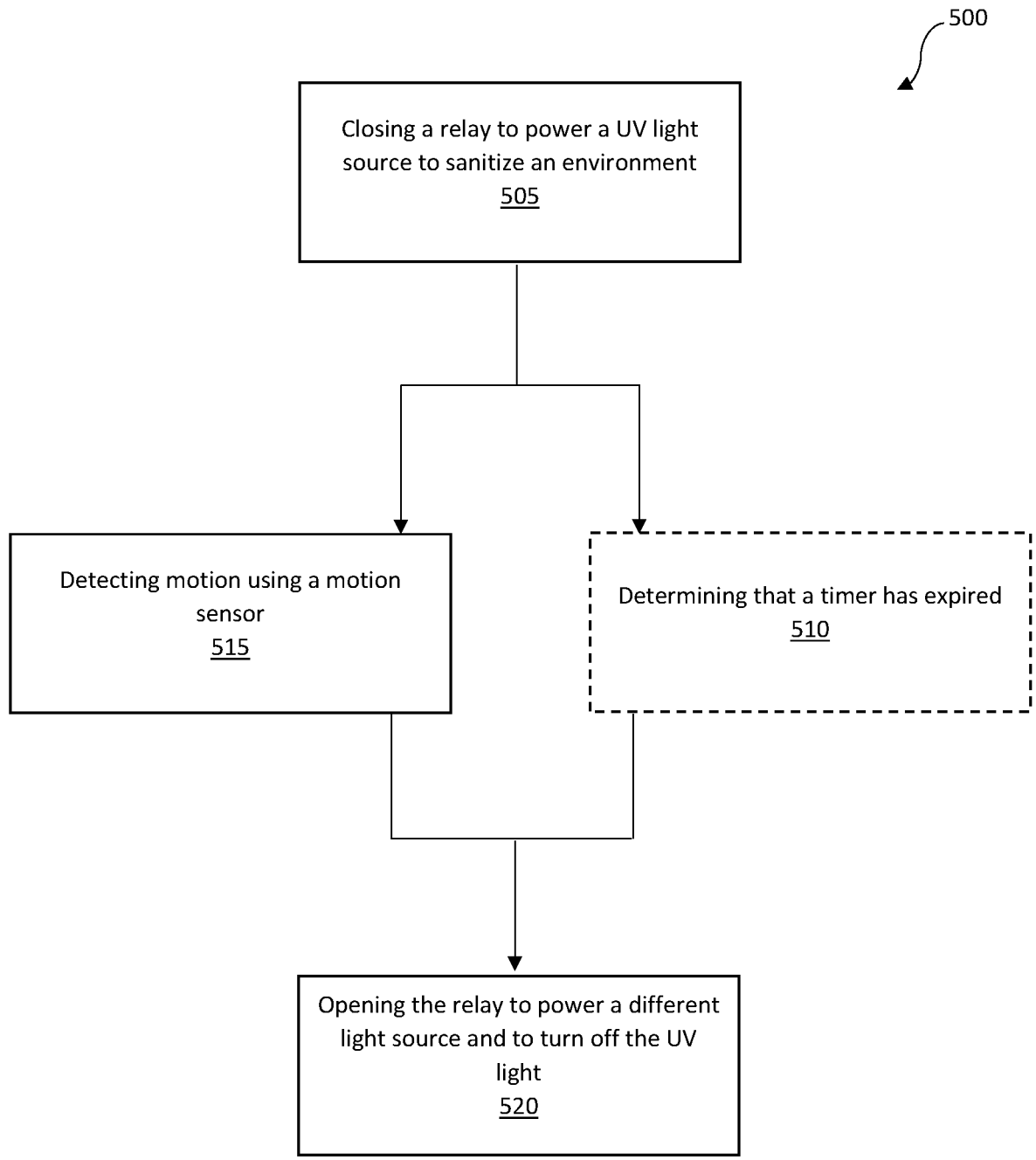
FIG. 5 depicts an exemplary sequence of steps of a process for automatically disabling a UV light source in a lighting assembly to prevent exposure of UV light to occupants according to embodiments of the present invention.

FIG. 5 depicts an exemplary sequence of steps of an electronically controlled process 500 for automatically disabling a UV light source in a lighting assembly to prevent exposure of UV light to occupants according to embodiments of the present invention. The lighting assembly can include an overhead lighting assembly having both visible and UV light sources and installed in a home, store, or office building, for example. Process 500 can be computer or electronic controlled, e.g., by a state-machine, processor, microcontroller, combinatorial logic, sequential circuits, or any suitable electronic control mechanism or combination of the above.

At step 505 of process 500, a relay of the lighting assembly is closed to power a UV light source (e.g., an LED) during a detected on period for UV light exposure. The UV light produced by the UV light source cleans and/or disinfects the surrounding environment (e.g., room), for example, to kill viruses, bacteria, germs, mold, etc. Step 505, for instance, can be triggered after a prescribed period of non-motion detected by a motion detector and measured by an on timer. Alternatively, step 505 can be triggered by an external signal indicating a safe period in which UV light can be exposed within a room. Alternatively, step 505 can be triggered by a combination of the above.

The duration of the UV production of Light source 3 is optionally controlled by a timer. The timer can be set for a predetermined duration (e.g., 30-45 minutes), or can include a dial or other input device that can be used to set a duration for producing UV light. The timer can be used to provide the desired amount of UV light and to prevent the UV light from being active when people are expected to enter the surrounding environment (e.g., an office, store, home, or other similar indoor environment). According to embodiments where the duration of the UV production of Light source 3 is controlled by a timer, at step 510, the lighting assembly determines that the timer has expired and enters step 520. According to some embodiments, the timer is included in the motion sensor. Alternatively, the timer can be external to the light fixture.

At step 515, while in the UV on duration, the motion sensor detects motion near the lighting assembly. The motion can indicate the presence of an occupant in the room where the lighting assembly is installed, or the presence of a person relatively close to the lighting assembly, for example. When motion is detected, step 520 is entered.

At step 520, responsive to the detected motion (step 515) or the expiration of a timer (step 510), the relay is opened to power a second light source (e.g., Light source 1 and/or Light source 2 depicted in FIGS. 1-4) and the UV Light source 3 correspondingly is turned off.

Figure 6:
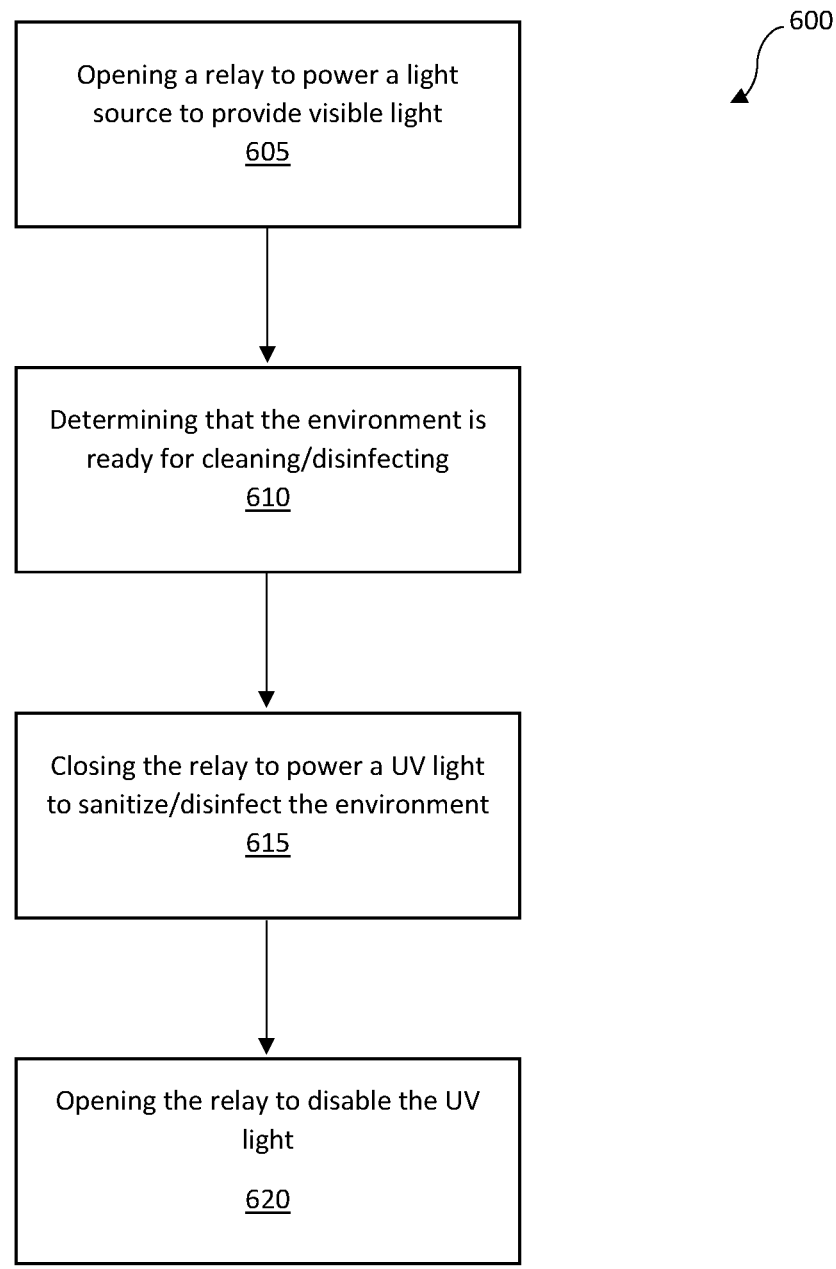
FIG. 6 depicts an exemplary sequence of steps of a process for automatically cleaning/disinfecting an environment using UV light using a lighting assembly and a motion detector according to embodiments of the present invention.

FIG. 6 depicts an exemplary sequence of steps of a process 600 for automatically cleaning/disinfecting an environment (e.g., room) using UV light using a lighting assembly and a motion detector according to embodiments of the present invention. The lighting assembly can be overhead lighting disposed in a home, store, or office building, for example. Process 600 can be computer or electronic controlled, e.g., by a state-machine, processor, microcontroller, combinatorial logic, sequential circuits, or any suitable electronic control mechanism or combination of the above.

At step 605, a relay of the lighting assembly is opened to power a light source that produces visible light. Step 605 can be triggered, e.g., by a light switch being manually selected to the on position and/or by a motion sensor sensing motion within a room.

At step 610, the lighting assembly determines that the environment is ready for cleaning/disinfecting. For example, step 610 can include determining that a timer is active (not yet expired). Moreover, step 610 can include a motion sensor determining that no motion has been detected in the room for a prescribed period of time.

At step 615, the relay is closed to power a UV light source (e.g., LED) that produces UV light to clean/disinfect the environment. At step 615 the visible light emitters can also be turned off. The UV "on" duration at step 615 can be timer based or could terminate upon motion being detected. Further, the UV "on" duration could be inhibited so that it only is triggered when the above is true and further when a secondary timer override indicates a safe period in which sanitation can take place.

At step 620, the relay is opened to disable the UV light indicating the end of the UV "on" duration. Step 620 can also include powering the visible light source(s) to produce visible light. Step 620 can be performed responsive to determining that a timer has expired or that motion has been detected by the overhead lighting assembly (e.g., by a motion sensor thereof).

Embodiments of the present invention are thus described. While the present invention has been described in particular embodiments, it should be appreciated that the present invention should not be construed as limited by such embodiments, but rather construed according to the following claims.

What is claimed is:

1. A method of automatically disabling an ultraviolet (UV) light source of a lighting assembly, the method comprising:
    closing a relay of the lighting assembly to power the UV light source of the lighting assembly, wherein the lighting assembly comprises a visible light source and the UV light source; and
    opening the relay to power the visible light source to produce visible light wherein said opening also correspondingly shuts off the UV light source.

2. The method of claim 1, further comprising determining that a timer associated with the lighting assembly expired and wherein said opening further comprises opening the relay responsive to the determining that the timer expired.

3. The method of claim 1, wherein the lighting assembly is operable to be an overhead lighting assembly for installation in a ceiling of an indoor environment.

4. The method of claim 1, wherein the visible light source comprises at least one of: a plurality of fluorescent lights and a plurality of visible light LED lights.

5. The method of claim 1, wherein the UV light source comprises a UV LED emitter.

6. The method of claim 1, further comprising opening the relay to power the visible light source to produce visible light, wherein said opening also correspondingly shuts off the UV light source, and wherein said opening is responsive to data produced by a sensor.

7. A lighting assembly comprising:
    a first light source configured to produce a first light;
    a second light source configured to produce a second light; and
    control circuitry for selectively powering the first light source and the second light source, said control circuitry comprising:
        a sensor;
        a relay coupled to the sensor and for selectively coupling a power source to one of: the first light source and second light source; and
        a timer,
    wherein the control circuitry automatically controls the relay to couple the relay to the first light source when the timer expires, automatically controls the relay to couple the relay to the second light source when the timer is active, and automatically controls the relay to couple the relay to the first light source according to a reading of the sensor.

8. The lighting assembly of claim 7, operable to be an overhead lighting assembly for installation in a ceiling of an indoor environment.

9. The lighting assembly of claim 7, wherein the first light source comprises at least one of: a plurality of fluorescent lights and a plurality of visible light LED lights.

10. The lighting assembly of claim 7, wherein the second light source comprises a UV LED emitter.

11. The lighting assembly of claim 7, further comprising an external switch and an external power source for powering the first light source, and wherein activating the external switch activates the first light source.

12. The lighting assembly of claim 7, further comprising a housing and wherein the motion sensor is integrated into the housing.

13. The lighting assembly of claim 7, wherein the timer is controlled by a remote wireless device.

14. A lighting assembly comprising:
    a first light source configured to produce a first light type;
    a second light source configured to produce a second light type; and
    control circuitry for selectively powering the first light source and the second light source, said control circuitry comprising:
        a sensor;
        a wireless transceiver; and
        a timer,
    wherein the control circuitry automatically receives a timer value from a wireless device using the wireless transceiver, controls the relay to couple the relay to the first light source when the timer value expires, automatically controls the relay to couple the relay to the second light source when the timer is active, and automatically controls the relay to couple the relay to the first light source according to a reading of the sensor.

15. The lighting assembly of claim 14, further comprising a safety timer that defines a safe period for the second light source, wherein the control circuitry controls the relay to couple the relay to the second light source only when both the timer and the safety timer are active.

16. The lighting assembly of claim 14, further comprising a third light source, wherein the control circuitry controls the relay to couple the relay to the first light source and the third light source when the timer value expires.

17. The lighting assembly of claim 14, operable to be an overhead lighting assembly for installation in a ceiling of an indoor environment.

18. The lighting assembly of claim 14, wherein the first light source comprises at least one of: a plurality of fluorescent lights and a plurality of visible light LED lights.

19. The lighting assembly of claim 14, wherein the second light source comprises a UV LED emitter.

20. The lighting assembly of claim 14, wherein the second light source produces a type of a light spectrum that kills viruses, germs, bacteria, and mold using a specific frequency of UV light or a specific duration of exposure.

* * * * *